United States Patent
He

(10) Patent No.: US 12,157,016 B2
(45) Date of Patent: Dec. 3, 2024

(54) ANTI-COLLISION SIMULATION DEVICE AND RADIOTHERAPY SYSTEM

(71) Applicants: SHENZHEN OUR NEW MEDICAL TECHNOLOGIES DEVELOPMENT CO., LTD., Shenzhen (CN); OUR UNITED CORPORATION, Xi'an (CN)

(72) Inventor: Bing He, Shenzhen (CN)

(73) Assignees: SHENZHEN OUR NEW MEDICAL TECHNOLOGIES DEVELOPMENT CO., LTD., Shenzhen (CN); OUR UNITED CORPORATION, Xi'an (CN)

(*) Notice: Subject to any disclaimer, the term of this patent is extended or adjusted under 35 U.S.C. 154(b) by 937 days.

(21) Appl. No.: 17/199,692

(22) Filed: Mar. 12, 2021

(65) Prior Publication Data
US 2021/0196983 A1 Jul. 1, 2021

Related U.S. Application Data

(63) Continuation-in-part of application No. PCT/CN2019/090997, filed on Jun. 12, 2019.

(30) Foreign Application Priority Data

Sep. 14, 2018 (CN) .......................... 201821510640.7

(51) Int. Cl.
*A61N 5/10* (2006.01)
(52) U.S. Cl.
CPC .... *A61N 5/1075* (2013.01); *A61N 2005/1076* (2013.01)
(58) Field of Classification Search
CPC .......... A61N 5/1075; A61N 2005/1076; A61N 5/1048
See application file for complete search history.

(56) References Cited

U.S. PATENT DOCUMENTS

| 5,878,112 A | 3/1999 | Koertge |
| 9,220,922 B2 * | 12/2015 | Morrow ............... A61N 5/1049 |

(Continued)

FOREIGN PATENT DOCUMENTS

| CN | 101254114 A | * | 9/2008 |
| CN | 101947360 A |  | 1/2011 |

(Continued)

OTHER PUBLICATIONS

International Search Report and Written Opinion issued in corresponding International Application No. PCT/CN2019/090997 mailed Aug. 30, 2019, with English translation.

*Primary Examiner* — Thaddeus B Cox
*Assistant Examiner* — Joshua Daryl D Lannu
(74) *Attorney, Agent, or Firm* — Morgan, Lewis & Bockius LLP

(57) ABSTRACT

An anti-collision simulation device and a radiotherapy system relate to the technical field of medical equipment. The anti-collision simulation device is applied to a radiotherapy device, and includes a supporting frame and a simulation rod rotatably connected to the supporting frame. A space enclosed by a rotation track of the simulation rod is matched with a space in a therapy cabin of the radiotherapy device. The supporting frame includes a fixing frame and a movable frame. The fixing frame is fixedly installed relative to the radiotherapy device. The simulation rod is rotatably connected to the movable frame, and the movable frame is able to move relative to the fixing frame, so as to enable the simulation rod to be located at different positions.

17 Claims, 5 Drawing Sheets

(56) References Cited

U.S. PATENT DOCUMENTS

| | | |
|---|---|---|
| 2011/0006230 A1 | 1/2011 | Fadler |
| 2013/0340165 A1 | 12/2013 | Dong et al. |
| 2020/0368555 A1 | 11/2020 | Gou et al. |

FOREIGN PATENT DOCUMENTS

| | | | |
|---|---|---|---|
| CN | 103429159 A | | 12/2013 |
| CN | 204864557 U | * | 12/2015 |
| CN | 108273199 A | | 7/2018 |

* cited by examiner

ANTI-COLLISION SIMULATION DEVICE AND RADIOTHERAPY SYSTEM

CROSS-REFERENCE TO RELATED APPLICATIONS

This disclosure is a Continuation-in-Part application of International Patent Application No. PCT/CN2019/090997 filed on Jun. 12, 2019, which claims priority to Chinese Patent Application No. 201821510640.7, filed with the Chinese Patent Office on Sep. 14, 2018, titled "ANTI-COLLISION SIMULATION DEVICE AND RADIOTHERAPY SYSTEM", which are incorporated herein by reference in their entirety.

TECHNICAL FIELD

The present disclosure relates to the technical field of medical equipment, and in particular, to an anti-collision simulation device and a radiotherapy system.

BACKGROUND

A gamma knife radiotherapy system utilizes a plurality of radioactive isotopes such as cobalt-60 to emit gamma rays from a plurality of directions, and the gamma rays intersect at an intersection point, thereby killing tumor cells at the intersection point and achieving the purpose of tumor radiotherapy.

As shown in FIG. 1, a gamma knife radiotherapy system in the prior art includes a therapy device 01 and a therapy couch 02. During a therapy, a patient lies on the therapy couch 02, and the therapy couch 02 can transport the patient into the therapy device 01, so that the therapy device 01 performs a radiation therapy on a diseased part (e.g., head) of the patient. Since the patient cannot be observed in the therapy device 01, in order to prevent the therapy device from colliding with a body part (e.g., head) of the patient, an anti-collision simulation of therapy is required to be performed on the patient before the patient enters the therapy device 01 for the radiation therapy, so as to avoid a collision risk in the therapy device 01. Specifically, as shown in FIG. 1, an anti-collision simulation device 03 includes a supporting rod 031 installed on the therapy device 01, and a simulation rod 032 rotatably connected to an upper end of the supporting rod 031. A space enclosed by a track of one rotation of the simulation rod 032 is equal to or slightly smaller than an inner space of the therapy device 01. In this way, before the patient enters the therapy device 01 for the radiation therapy, the anti-collision simulation device 03 is installed at a corresponding position (generally, the therapy device 01), and after the anti-collision simulation device 03 is adjusted, the simulation rod 032 is swung to see whether the simulation rod 032 collides with the patient. After the anti-collision simulation is completed, the anti-collision simulation device 03 is removed since the anti-collision simulation device 03 affects the movement of the therapy couch 02.

However, in the gamma knife radiotherapy system in the prior art, the anti-collision simulation device 03 needs to be installed and removed before each therapy, and the anti-collision simulation device 03 needs to be manually adjusted. It is inconvenient and takes a long time to remove, install, and operate the anti-collision simulation device 03, which increase the time for a doctor to be beside the gamma knife radiotherapy system, and thus the doctor receives the scattered radiation of the radiotherapy system for a long time, which is not conducive to the doctor's health.

SUMMARY

In one aspect, embodiments of the present disclosure provide an anti-collision simulation device. The anti-collision simulation device includes a supporting frame and a simulation rod rotatably connected to the supporting frame. The supporting frame includes a fixing frame and a movable frame. The simulation rod is rotatably connected to the movable frame, and the movable frame is able to move relative to the fixing frame, so as to enable the simulation rod to be located at different positions.

In another aspect, the embodiments of the present disclosure further provide a radiotherapy system. The radiotherapy system includes the above anti-collision simulation device, a radiotherapy device and a therapy couch. The movable frame of the anti-collision simulation device is able to move relative to the fixing frame, so as to enable the simulation rod to be located at different positions in a vertical direction relative to the therapy couch. A space enclosed by a rotation track of the simulation rod is matched with a space in a therapy cabin of the radiotherapy device. The fixing frame is fixedly installed relative to the radiotherapy device.

BRIEF DESCRIPTION OF DRAWINGS

In order to describe technical solutions in the embodiments of the present disclosure or in the prior art more clearly, the accompanying drawings to be used in the description of the embodiments or the prior art will be briefly described below. Obviously, the accompanying drawings to be described below are merely accompanying drawings of some embodiments of the present disclosure, and a person of ordinary skill in the art may obtain other drawings according to these drawings without paying any creative effort.

DETAILED DESCRIPTION

Technical solutions in the embodiments of the present disclosure will be described clearly and completely with reference to the accompanying drawings in the embodiments of the present disclosure. Obviously, the described embodiments are merely some but not all embodiments of the present disclosure. All other embodiments obtained by a person of ordinary skill in the art on the basis of the embodiments of the present disclosure without paying any creative effort shall be included in the protection scope of the present disclosure.

Terms such as "first" and "second" are only used for descriptive purposes, and are not to be construed as indicating or implying the relative importance or implicitly indicating the number of indicated technical features. Thus, a feature defined by "first" or "second" may explicitly or implicitly include one or more of the features. In the description of the embodiments of the present disclosure, "a plurality of/the plurality of" means two or more unless otherwise specified.

In the description of the embodiments of the present disclosure, it will be noted that the terms "installed", "communicated", "connected" should be understood in a broad sense unless otherwise expressly specified or defined, for example, it may be a fixed connection, a detachable connection or an integral connection. Specific meanings of the above terms in the embodiments of the present disclosure may be understood by a person of ordinary skill in the art according to specific situations.

Figure 2:
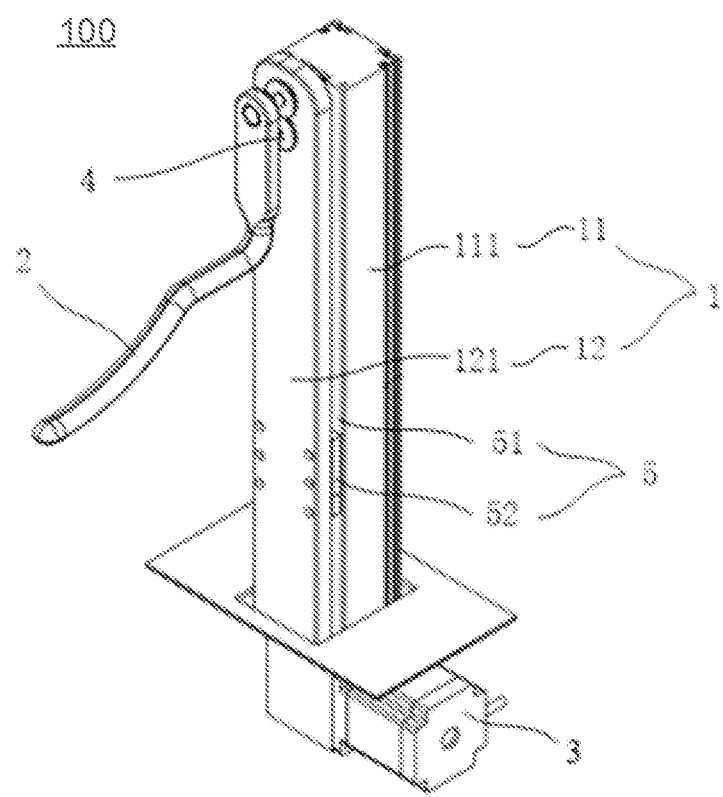
FIG. 2 is a schematic structural diagram of an anti-collision simulation device in accordance with the embodiments of the present disclosure.
Figure 3:
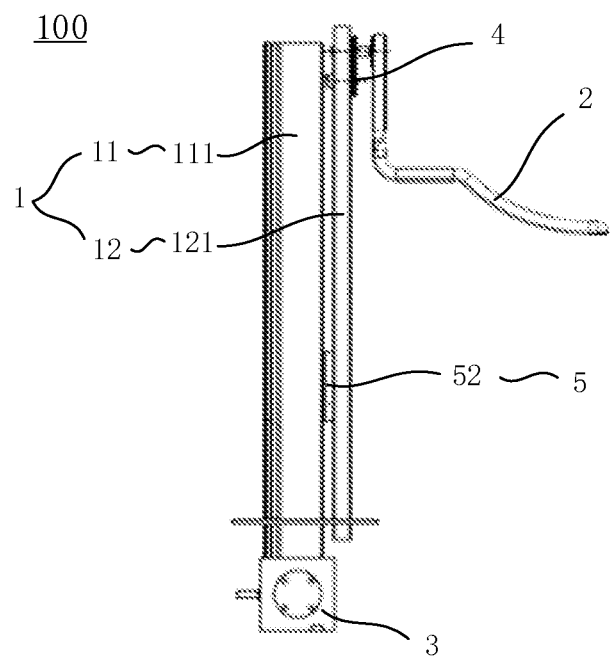
FIG. 3 is a schematic structural side view of an anti-collision simulation device in accordance with the embodiments of the present disclosure.

The embodiments of the present disclosure provide an anti-collision simulation device 100. As shown in FIGS. 2, 3 and 8, the anti-collision simulation device 100 may be applied to a radiotherapy device 600, and includes a supporting frame 1 and a simulation rod 2 rotatably connected to the supporting frame 1. A space enclosed by a rotation track of the simulation rod 2 is matched with a space in a therapy cabin of the radiotherapy device 600. The supporting frame 1 includes a fixing frame 11 and a movable frame 12. The fixing frame 11 is fixedly installed relative to the radiotherapy device, the simulation rod 2 is rotatably connected to the movable frame 12, and the movable frame 12 is able to move relative to the fixing frame 11, so as to enable the simulation rod 2 to be located at different positions.

In the anti-collision simulation device of the embodiments of the present disclosure, as shown in FIGS. 2 and 3, the supporting frame 1 includes the fixing frame 11 and the movable frame 12, and the simulation rod 2 is rotatably connected to the movable frame 12, and the fixing frame 11 is fixedly installed relative to the radiotherapy device. Thus, the movable frame 12 is able to move relative to the fixing frame 11, so as to enable the simulation rod 2 to be located at different positions. In this way, when an anti-collision simulation is needed, as long as the movable frame 12 moves relative to the fixing frame 11 to enable the simulation rod 2 to be located at a working position, and then the simulation rod 2 rotates to perform the anti-collision simulation. After the anti-collision simulation is completed, the movable frame 12 moves relative to the fixing frame 11 again to enable the simulation rod 2 to be located at another position, such as a hidden position. In this case, the anti-collision simulation device will not interfere with and block a movement of the therapy couch. Compared with the prior art, after the fixing frame 11 is fixedly installed relative to the radiotherapy device, the movable frame 12 is able to move relative to the fixing frame 11, so as to enable the simulation rod 2 to be located at different positions, and then a corresponding anti-collision simulation and a corresponding therapy couch movement may be performed according to the different positions of the simulation rod 2. Thus, the anti-collision simulation device does not need to be frequently installed and removed, the operation is convenient and simple, and a position of the anti-collision simulation device fixedly installed relative to the radiotherapy device is fixed, which is convenient for positioning the simulation rod 2. Therefore, the anti-collision simulation may be rapidly performed to reduce the time for a doctor to be beside the radiotherapy system and reduce the damage to the doctor's health.

It will be noted that, when a patient is subject to a radiation therapy, a corresponding diseased part (e.g., head) of the patient is placed in the therapy cabin of the radiotherapy device. The space in the therapy cabin is generally in a semi-circular shape, and therapy rays are emitted from radiation source devices that are uniformly distributed to treat the diseased part of the patient. The space enclosed by the rotation track of the simulation rod 2 is matched with the space in the therapy cabin of the radiotherapy device, which is equivalent to the rotation of the simulation rod 2 simulating the space in the therapy cabin of the radiotherapy device. Thus, if the patient does not collide with the simulation rod 2, the patient will not collide with the therapy cabin when entering the therapy cabin for therapy. The space enclosed by the rotation track of the simulation rod 2 is matched with the space in the therapy cabin of the radiotherapy device, which may be that a size of the space enclosed by the rotation track of the simulation rod 2 may be completely same as a size of the space in the therapy cabin or less than a preset offset threshold of the space in the therapy cabin. The anti-collision simulation device 100 in the embodiments of the present disclosure is applied to the radiotherapy device, and the fixing frame 11 is fixedly installed relative to the radiotherapy device, which means that the anti-collision simulation device 100 is used in combination with the radiotherapy device. In some examples, the anti-collision simulation device 100 may be installed and fixed on the radiotherapy device, or the anti-collision simulation device 100 may be fixed elsewhere (e.g., fixed on the ground beside the radiotherapy device). In addition, the different positions at which the simulation rod 2 is able to be located refer to positions determined with reference to a rotation center of the simulation rod 2, which has nothing to do with a rotation angle of the simulation rod 2. The different positions at least include the working position and the hidden position. The working position refers to a relative position of the space enclosed by the rotation track of the simulation rod 2 and the patient on the therapy couch, which is consistent with a relative position of the patient and the therapy cabin when the patient is treated in the therapy cabin of the radiotherapy device. In this case, the anti-collision simulation may be performed. The hidden position means that the simulation rod 2 does not interfere with the movement of the therapy couch when the simulation rod 2 moves out of a motion track of the therapy couch along with the movable frame 12. For example, in general, the simulation rod 2 is above the therapy couch when being located at the working position, and is below the therapy couch when being located at the hidden position.

The movement of the movable frame 12 relative to the fixing frame 11 may be manually operated or automatically controlled by a driving device. In a case of automatically controlling the movement of the movable frame 12 relative to the fixing frame 11 by using the driving device, the doctor may control the movement of the movable frame 12 relative to the fixing frame 11 in a control room isolated from a therapy room, thereby reducing the time of the doctor in the therapy room and reducing a radiation risk to the doctor. Therefore, the anti-collision simulation device in this embodiment further includes a first driving device 3. The first driving device 3 is connected to the movable frame 12, and is used for driving the movable frame 12 to move relative to the fixing frame 11.

Of course, the rotation of the simulation rod 2 may also be manually operated or automatically controlled by a driving device. Similarly, in a case where the rotation of the simulation rod 2 is automatically controlled by the driving device, the doctor may control the rotation of the simulation rod 2 in the control room to perform an automatic simulation when the simulation rod 2 is located at the working position, thereby reducing the time of the doctor in the therapy room and reducing the radiation risk to the doctor. Therefore, the anti-collision simulation device in this embodiment further includes a second driving device 4. The second driving device 4 is connected to the simulation rod 2 for driving the simulation rod 2 to rotate.

It will be noted that the first driving device 3 may be solely provided to facilitate the operation of the movable frame 12 at different positions. The second driving device 4 may also be solely provided to facilitate the rotating operation of the simulation rod 2. Both the first driving device 3 and the second driving device 4 may also be provided, so that after positioning the patient, the doctor may move the simulation rod 2 along with the movable frame 12 to different positions and control the rotation of the simulation rod 2 in the control room, which completely realizes an automatic anti-collision simulation, thereby greatly reducing the time of the doctor in the therapy room and reducing the radiation risk.

The movable frame 12 may move relative to the fixing frame 11 in various implementation manners, such as a curvilinear motion (e.g., rotation) and a linear motion (e.g., sliding), as long as the simulation rod 2 is able to be located at different positions (the hidden position or the working position). It is preferable that the movable frame 12 may move linearly relative to the fixing frame 11. As is known, the fixing frame 11 and the movable frame 12 are slidably connected through a sliding mechanism 5, so that the movable frame 12 may move linearly relative to the fixing frame 11.

In some embodiments, referring to FIGS. 2 and 3, the fixing frame 11 includes a fixing frame body 111 and a guide 51 disposed on the fixing frame body 111, and the movable frame 12 includes a movable frame body 121 and a slider 52 disposed on the movable frame body 121. Or, the fixing frame 11 includes a fixing frame body 111 and a slider 52 disposed on the fixing frame body 111, and the movable frame 12 includes a movable frame body 121 and a guide 51 disposed on the movable frame body 121. The guide 51 and the slider 52 constitute the sliding mechanism 5.

The guide 51 may be cooperated with the slider 52 in various implementation manners, for example, in an implementation manner of a guide rail and a sliding block, or in an implementation manner of a guide pillar and a guide sleeve. In some embodiments, referring to FIGS. 2 and 3, the guide 51 of the sliding mechanism 5 is the guide rail, and the slider 52 is the sliding block that is able to slide in cooperation with the guide rail.

Or, the guide 51 is the guide pillar, and the slider 52 is the guide sleeve that is able to slide in cooperation with the guide pillar.

The first driving device 3 may be a motor (including a linear motor and a rotary motor), a pneumatic cylinder, or a hydraulic cylinder, etc. In a form of a driving force directly provided by the first driving device 3, the linear motor, the pneumatic cylinder, or the hydraulic cylinder may provide a linear driving force, and the rotary motor may provide a rotary driving force. Thus, in a case where the movable frame 12 is required to perform the curvilinear motion (e.g., rotation) relative to the fixing frame 11, if the first driving device 3 is the linear motor, the pneumatic cylinder, or the hydraulic cylinder, a corresponding mechanism is required to convert the linear driving force into the rotary driving force. If the first driving device 3 is the rotary motor, the movable frame 12 may be directly driven to rotate. Similarly, in a case where the movable frame 12 is required to perform the linear motion (e.g., sliding) relative to the fixing frame 11, if the first driving device 3 is the linear motor, the pneumatic cylinder, or the hydraulic cylinder, the movable frame 12 may be directly driven to perform the linear motion. If the first driving device 3 is the rotary motor, a corresponding mechanism is required to convert the rotary driving force into the linear driving force. Specific implementation manners will be described below by taking an example in which the movable frame 12 performs the linear motion (e.g., sliding) relative to the fixing frame 11.

If the first driving device is the linear motor, the pneumatic cylinder, or hydraulic cylinder, the movable frame 12 may be directly driven to move linearly. In some embodiments, the first driving device 3 is the pneumatic cylinder or the hydraulic cylinder, a piston rod of the pneumatic cylinder or the hydraulic cylinder is fixedly connected to the movable frame 12, and a cylinder body of the pneumatic cylinder or the hydraulic cylinder is fixed relative to the fixing frame 11. Or, the first driving device 3 is the linear motor, a rotor of the linear motor is fixedly connected to the movable frame 12, and a stator of the linear motor is fixed relative to the fixing frame 11. The cylinder body of the pneumatic cylinder or the hydraulic cylinder and the stator of the linear motor are fixed relative to the fixing frame 11, which may be directly fixed on the fixing frame 11, and may also be fixed on other positions or devices with an unchanged position relative to the fixing frame 11.

If the first driving device 3 is the rotary motor, the corresponding mechanism is required to convert the rotary driving force into the linear driving force. Therefore, the anti-collision simulation device 100 further includes a transmission mechanism that is connected to the rotary motor and used for changing the rotary motion into the linear motion. The transmission mechanism is connected to the movable frame 12 and used for driving the movable frame 12 to move linearly relative to the fixing frame 11 under an action of the rotary motor.

In some embodiments, the transmission mechanism includes a rotary motion member and a linear motion member that are cooperated with each other. The rotary motion member is connected to an output shaft of the rotary motor, and the linear motion member is connected to the movable frame 12.

The rotary motion member may be cooperated with the linear motion member in various implementation manners, for example, in an implementation manner of a ball screw mechanism, or in an implementation manner of a rack-and-pinion mechanism. That is, the rotary motion member of the transmission mechanism is a screw shaft, and the linear motion member is a nut that is cooperated with the screw shaft.

Or, the rotary motion member is a pinion, and the linear motion member is a rack that is cooperated with the pinion.

It will be noted that the second driving device 4 is used for driving the simulation rod 2 to rotate. For convenience of layout and cost saving, the rotary motor is generally used for driving.

When the simulation rod 2 performs the anti-collision simulation, the simulation rod 2 rotates, and if the simulation rod 2 is found to collide with the patient, a position of the patient needs to be adjusted. However, this simulation method cannot avoid the collision of the simulation rod 2 with the patient. Therefore, in order to avoid the collision of the simulation rod 2 with the patient during the anti-collision simulation, a sensing device may be provided on the simulation rod 2, and the sensing device is utilized to obtain a distance information of the simulation rod 2 and the patient, so as to know whether the simulation rod 2 will collide with the patient if it continues rotating according to the distance information. If it is found that the simulation rod 2 will collide with the patient in a case where the simulation rod 2 continues rotating, it is indicated that the position of the patient needs to be adjusted. In this case, as long as the rotation of the simulation rod 2 is stopped, the simulation rod 2 will not collide with the patient.

Figure 5A:
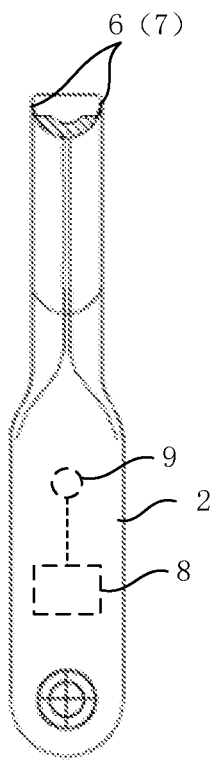
FIGS. 5A and 5B are schematic structural diagrams of a simulation rod of an anti-collision simulation device, in which a portion of the simulation rod is made of a flexible material, in accordance with the embodiments of the present disclosure.

The sensing device is provided to prevent the simulation rod 2 from colliding with the patient in various specific implementation manners. For example, in a case where the simulation rod 2 is manually operated, the sensing device may be enabled to send out a prompt signal to prompt the doctor to stop rotating the simulation rod 2. In some embodiments, as shown in FIG. 5A, the anti-collision simulation device 100 further includes a first sensing device 6, a first controller 8 and a prompter 9 that are electrically connected. The first sensing device 6 is disposed on the simulation rod 2, and used for obtaining the distance information of the simulation rod 2 and the patient and sending the distance information to the first controller 8. The first controller 8 is used for controlling the prompter 9 to send out the prompt signal according to the distance information obtained by the first sensing device. The first sensing device may include a sensor and a transmitter that is in communication with the sensor. The sensor obtains the distance information of the simulation rod 2 and the patient, and the transmitter sends the distance information to the first controller 8. The first controller 8 may be a control circuit, such as a PLC circuit. The prompt signal may be a sound made by a buzzer, a light ray emitted from an indicator light, or an image displayed on a display screen, or the like.

Figure 5B:
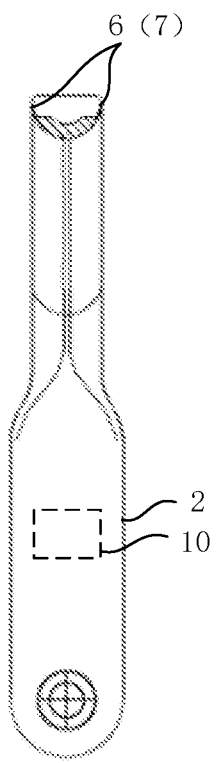

In a case where the simulation rod 2 is automatically operated through the second driving device 4, as shown in FIG. 5B, the anti-collision simulation device 100 further includes a second sensing device 7, and a second controller 10 that is electrically connected to the second driving device and the second sensing device 7. The second sensing device 7 is disposed on the simulation rod 2, and used for obtaining the distance information of the simulation rod 2 and the patient and sending the distance information to the second controller 10. The second controller 10 is used for controlling the second driving device to drive the simulation rod 2 to run in a state according to the distance information sent by the second sensing device 7. The second driving device driving the simulation rod 2 to run in a state is to control the simulation rod 2 to rotate or stop. The second sensing device 7 may be the same as the first sensing device 6 or different from the first sensing device 6. The second controller 10 may be the same as the first controller 8 or different from the first controller 8. For example, the second sensing device 7 may include a sensor and a transmitter that is in communication with the sensor. The sensor obtains the distance information of the simulation rod 2 and the patient, and the transmitter sends the distance information to the second controller 10. The second controller 10 may be a control circuit for driving the simulation rod 2 to run in a state, such as a PLC circuit.

Generally, when the simulation rod 2 rotates to perform the anti-collision simulation, if a collision occurs, the patient may first be hit by a side (an inner side) of the simulation rod 2 proximate to the patient. In order to reduce an injury caused by a fact that the simulation rod 2 may collide with the patient, referring to FIGS. 4 and 5, the inner side of the simulation rod 2 is made of a flexible material. The flexible material may buffer an impact brought by collision well, and effectively avoid the injury to the patient when the simulation rod 2 collides with the patient. In addition, for a medical equipment, the flexible material is preferably a medical silica gel.

It will be noted that, in order to ensure that the simulation rod 2 does not deform when it rotates, which results in a large deviation generated between the space formed by the rotation track of the simulation rod 2 and a space actually needed, only a side of the simulation rod 2 facing the space formed by the rotation track is made of the flexible material. Other parts of the simulation rod 2 may be made of a material with a higher strength to ensure a structural strength of the simulation rod 2, for example, made of a high-strength aluminum alloy, and an outer surface thereof is hard anodized to ensure that the simulation rod 2 does not deform.

Figure 6:
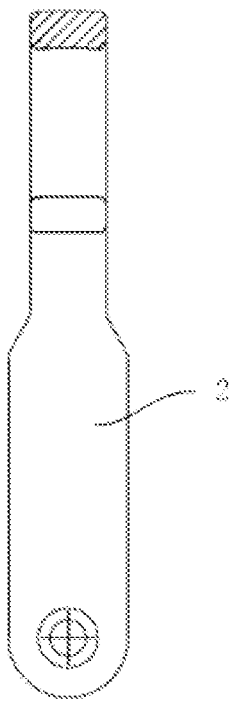
FIG. 6 is a schematic structural diagram of a simulation rod of an anti-collision simulation device, in which a cross section of the simulation rod is in a rectangular shape, in accordance with the embodiments of the present disclosure.
Figure 7:
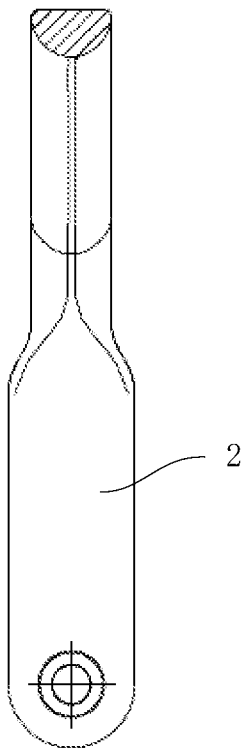
FIG. 7 is a schematic structural diagram of a simulation rod of an anti-collision simulation device, in which a cross section of the simulation rod is in a semi-circular shape, in accordance with the embodiments of the present disclosure.

A cross section of the simulation rod 2 is in various shapes, and for example, as shown in FIG. 6, in an approximately rectangular shape or in a shape in which the side of the simulation rod 2 facing the space formed by the rotation track of the simulation rod 2 is recessed inward. However, the simulation rod 2 collides with the patient directly, and is in surface contact with the patient, which has a large impact on the patient. Therefore, in order to alleviate the injury to the patient when the simulation rod 2 collides with the patient, as shown in FIGS. 5A, 5B and 7, the cross section of the simulation rod 2 is in a semi-circular shape, and an arc convex surface of the semi-circular shape is located on the inner side of the simulation rod 2. In this way, the simulation rod 2 is in progressive linear contact with the patient, which effectively alleviates the injury to the patient when the simulation rod 2 collides with the patient.

Figure 4:
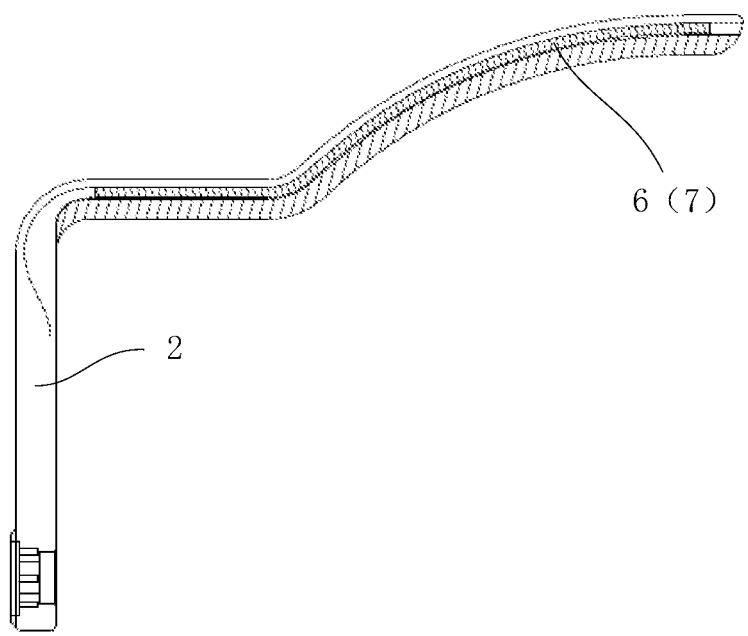
FIG. 4 is a schematic structural side view of a simulation rod of an anti-collision simulation device in accordance with the embodiments of the present disclosure.

It will be noted that the first sensing device 6 and the second sensing device 7 are provided on the simulation rod 2, and preferably, on the side (the inner side) of the simulation rod 2 proximate to the patient. However, since the inner side of the simulation rod 2 is made of the flexible material to avoid a large injury to the patient, as shown in FIGS. 4 and 5, the first sensing device 6 and the second sensing device 7 are respectively disposed on two sides of the simulation rod 2 rather than on the inner side of the simulation rod 2. In addition, the first sensing device 6 and the second sensing device 7 are used for obtaining the distance information of the simulation rod 2 and the patient, and the sensor of the first sensing device 6 or the second sensing device 7 may be an infrared sensor, a laser sensor, or the like.

Figure 8A:
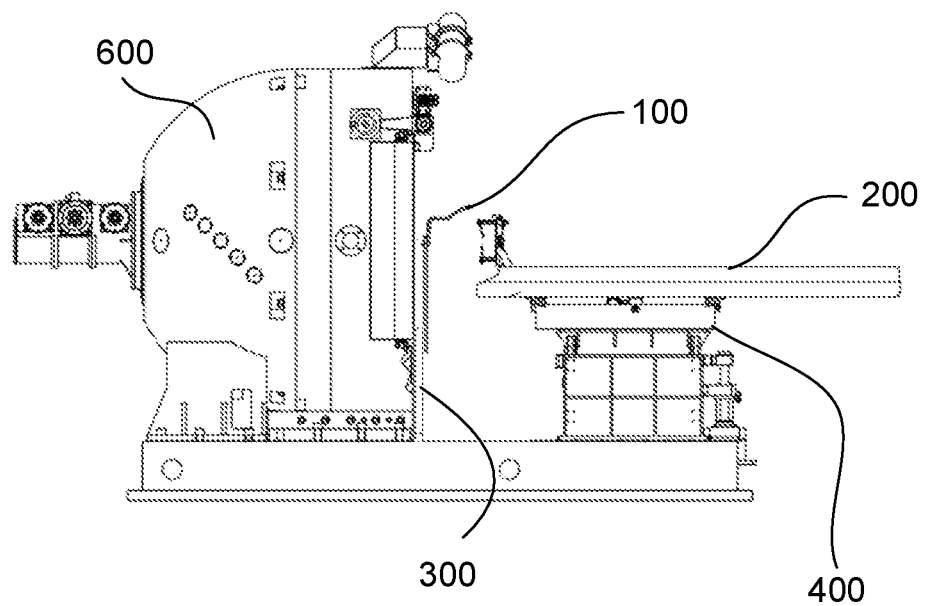
FIGS. 8A and 8B are schematic structural diagrams of a radiotherapy system in accordance with the embodiments of the present disclosure.

In another aspect, the embodiments of the present disclosure further provide a radiotherapy system. As shown in FIG. 8A, the radiotherapy system includes the anti-collision simulation device 100, the radiotherapy device 600 and a therapy couch 200. The movable frame 12 of the anti-collision simulation device 100 is able to move relative to the fixing frame 11, so as to enable the simulation rod 2 to be located at different positions in a vertical direction relative to the therapy couch 200. The space enclosed by the rotation track of the simulation rod 2 is matched with the space in the therapy cabin of the radiotherapy device 600. The fixing frame is fixedly installed relative to the radiotherapy device 600.

The radiotherapy system in the embodiments of the present disclosure includes the anti-collision simulation device 100, the radiotherapy device 600 and the therapy couch 200, and the movable frame 12 of the anti-collision simulation device 100 is able to move relative to the fixing frame 11, so as to enable the simulation rod 2 to be located at the different positions in the vertical direction relative to the therapy couch 200. In this way, when an anti-collision simulation is performed, as long as the movable frame 12 moves relative to the fixing frame 11 to enable the simulation rod 2 to be located at a working position, and in this case, the simulation rod 2 rotates to perform the anti-collision simulation. After the anti-collision simulation is completed, the movable frame 12 moves relative to the fixing frame 11 again to enable the simulation rod 2 to be located at another position, such as a hidden position, and in this case, the anti-collision simulation device 100 will not interfere with and block the movement of the therapy couch 200. Compared with the prior art, the anti-collision simulation device 100 does not need to be frequently installed and removed, the operation is convenient and simple, and a position of the anti-collision simulation device 100 fixed relative to the radiotherapy device is relatively fixed, which is convenient for positioning. Therefore, the operation is simple and convenient, and the anti-collision simulation may be rapidly performed to reduce the time for a doctor to be beside the radiotherapy system and reduce the damage to the doctor's health.

Figure 8B:
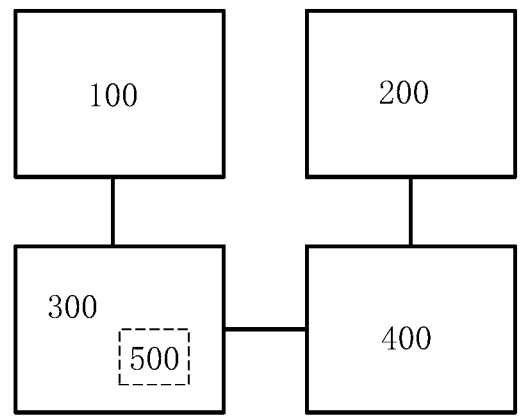

In order to prevent the simulation rod 2 of the anti-collision simulation device 100 from colliding with the radiotherapy device caused by a misoperation in an actual operation when the simulation rod 2 of the anti-collision simulation device 100 is located at the working position and the therapy couch carries the patient, referring to FIGS. 8A and 8B, in an embodiment of the radiotherapy system in the embodiments of the present disclosure, the radiotherapy system further includes an anti-collision control device 300 and a therapy couch control device 400 that are electrically connected to each other. The anti-collision control device 300 is used for sending different control instructions to the therapy couch control device 400 according to different positions of the simulation rod 2 of the anti-collision simulation device 100. The therapy couch control device 400 is used for controlling the therapy couch 200 to move correspondingly according to the received control instructions.

In some examples, the anti-collision control device 300 includes a sensor, a processor and a transmitter that are in communication connection. The sensor obtains the position information of the simulation rod 2, and the processor processes the position information of the simulation rod 2 and generates a control instruction. The transmitter sends the control instruction to the therapy couch control device 400.

In some examples, the therapy couch control device 400 includes a receiver, a controller, and a driving device that are connected. The receiver receives the control instruction sent by the transmitter, and the controller controls the driving device to drive the therapy couch 200 to move according to the control instruction. The driving device may be the same as the first driving device or the second driving device.

Sending the different control instructions to the therapy couch control device 400, includes: when it is found that a position of the simulation rod 2 of the anti-collision simulation device 100 blocks the movement of the therapy couch 200, sending an alarm instruction or a prohibition instruction to prevent the therapy couch control device 400 from controlling the therapy couch 200 to move, so as to make the therapy couch 200 stationary, and when it is found that the position of the simulation rod 2 of the anti-collision simulation device 100 does not block the movement of the therapy couch 200, sending a safety instruction or a driving instruction to allow the therapy couch control device 400 to control the therapy couch 200 to move, and in this case, the therapy couch 200 may move.

In another embodiment of the radiotherapy system in the embodiments of the present disclosure, referring to FIGS. 8A and 8B, the radiotherapy system further includes an anti-collision control device 300 and a therapy couch control device 400 that are electrically connected to each other. The anti-collision control device 300 is used for sending a position information of the simulation rod 2 of the anti-collision simulation device 100 to the therapy couch control device 400. The therapy couch control device 400 is used for controlling the therapy couch 200 to move correspondingly according to the position information.

The anti-collision control device 300 sends only the position information of the simulation rod 2 of the anti-collision simulation device 100 to the therapy couch control device 400, and the therapy couch control device 400 judges whether it controls the therapy couch 200 to move according to the position information of the simulation rod 2 of the anti-collision simulation device 100.

Therefore, by providing the anti-collision control device 300 and the therapy couch control device 400, the therapy couch 200 may be prevented from colliding with the anti-collision simulation device 100.

It will be noted that the position information of the simulation rod 2 of the anti-collision simulation device 100 includes the working position and the hidden position, and may be determined by detecting a position of a rotation center of the simulation rod 2 of the anti-collision simulation device 100 by utilizing a detecting device (e.g., an infrared sensor).

The position information of the simulation rod 2 of the anti-collision simulation device 100 may be obtained in various implementation manners. For example, since the anti-collision control device 300 is used to control the movement of the movable frame 12 of the anti-collision simulation device 100, the position information of the simulation rod 2 of the anti-collision simulation device 100 may be obtained according to the movement information of the movable frame 12. In some examples, the anti-collision control device 300 includes a sensor, a transmitter, and a driving device that are connected, and the driving device is connected to the movable frame 12 of the anti-collision simulation device 100. The driving device is used to drive the movable frame 12 to move. The sensor obtains the position information of the simulation rod 2 according to the movement information of the movable frame 12, and the transmitter sends the position information of the simulation rod 2 to the therapy couch control device 400. Or, the radiotherapy system further includes a position detecting device 500, and the position information of the simulation rod 2 of the anti-collision simulation device 100 is directly obtained by the position detecting device 500. The position detecting device 500 may be a sensor, such as infrared sensor. In some examples, the anti-collision control device 300 includes a transmitter that is in communication with the position detecting device 500. The transmitter sends the position information of the simulation rod 2 obtained by the position detecting device 500 to the therapy couch control device 400.

In some examples, the therapy couch control device 400 includes a receiver, a chip, a controller, and a driving device that are connected. The receiver receives the position information of the simulation rod 2 sent by the transmitter, the chip makes a judgment on the position information of the simulation rod 2, and the controller controls the driving device to drive the therapy couch 200 to move according to the judgment result. The driving device of the anti-collision control device 300 or the therapy couch control device 400 may be the same as the first driving device or the second driving device.

In order to prevent the therapy couch 200 from colliding with the anti-collision simulation device 100 more accurately, a path information of the therapy couch 200 to move may be combined on a basis of the position information of the simulation rod 2 of the anti-collision simulation device 100, so as to judge whether a collision will occur, which makes the judgment more accurate. For example, the therapy couch control device 400 determines whether the simulation rod 2 is on a movement path of the therapy couch 200 in a movement direction according to the position information of the simulation rod 2 and a position information of the therapy couch 200. If so, the therapy couch 200 is controlled to stop moving. If not, the therapy couch 200 is controlled to move.

Further, if the therapy couch control device 400 finds that the position of the simulation rod 2 is located on the movement path of the therapy couch 200 in the movement direction, it may be that the therapy couch control device 400 sends an instruction to the anti-collision control device 300 to make the anti-collision control device 300 control the movable frame 12 of the anti-collision simulation device 100 to move, so as to enable the simulated rod 2 to move to the hidden position without colliding with the therapy couch 200.

Or, if the therapy couch control device 400 finds that the position of the simulation rod 2 is located on the movement path of the therapy couch 200 in the movement direction, the therapy couch control device 400 gives an alarm message to display a movement disorder, and the doctor sends an instruction to the anti-collision control device.

In addition, it will be noted that the anti-collision control device 300 is an upper computer of the first driving device 3 of the anti-collision simulation device 100, and a signal is sent to the first driving device 3 through the anti-collision control device 300, so that the first driving device 3 drives the movable frame 12 to move, so as to realize the different positions of the simulation rod 2.

Figure 1:
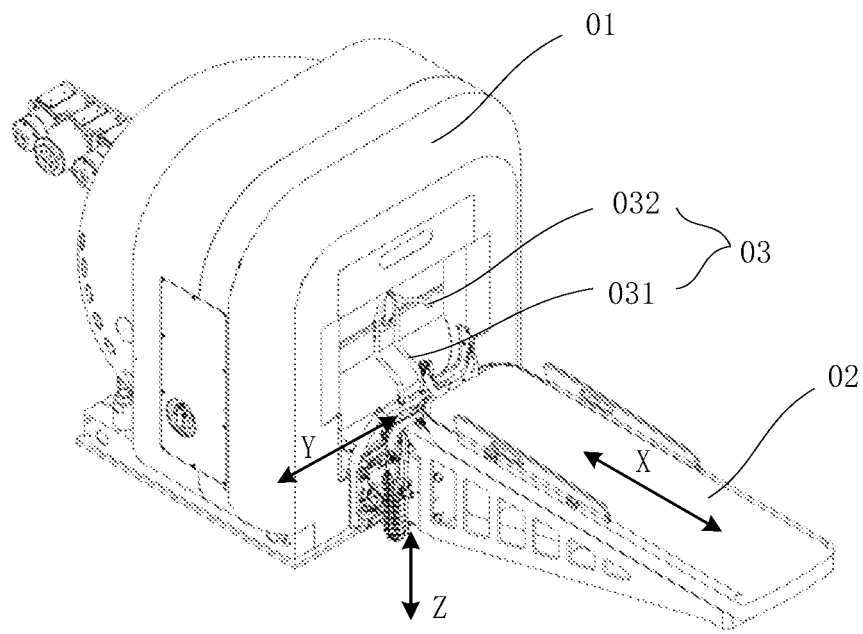
FIG. 1 is a schematic structural diagram of a gamma knife radiotherapy system in the prior art.

It will be noted that, a general therapy couch 200 may realize a motion in three-dimensional directions (X direction, Y direction and Z direction of the three-dimensional coordinate system as shown in FIG. 1). In a case where the simulation rod 2 of the anti-collision simulation device 100 is not located at the hidden position, a collision caused by a motion in the Y direction is common, but a collision caused by a motion in another direction is not excluded. Therefore, in the radiotherapy system in the embodiments of the present disclosure, the anti-collision control device 300 may prevent all possible collisions between the anti-collision simulation device 100 and the therapy couch 200 in three-dimensional directions.

In addition, in order to make the radiotherapy system more beautiful, the anti-collision simulation device 100 may be designed as an independent industrial model. Or, the anti-collision simulation device 100 may be integrated with industrial models of other structures of the radiotherapy system. For example, the supporting frame 1 (or the fixing frame 11) of the anti-collision simulation device 100 may be integrated with the industrial models of other structures. Furthermore, in order to avoid inconvenience caused by exposure of the simulation rod 2 of the anti-collision simulation device 100, a receiving groove that may receive the simulation rod 2 may further be provided at a corresponding position of the radiotherapy system.

The above descriptions are merely specific implementation manners of the present application, but the protection scope of the present application is not limited thereto. Changes or replacements that any person skilled in the art could readily conceive of within the technical scope of the present application shall be included in the protection scope of the present application. Therefore, the protection scope of the present application shall be subject to the protection scope of the claims.

What is claimed is:

1. An anti-collision simulation device, comprising:
   a supporting frame;
   a simulation rod rotatably connected to the supporting frame, wherein the supporting frame includes a fixing frame and a movable frame, the simulation rod is rotatably connected to the movable frame, and the movable frame is able to move relative to the fixing frame, so as to enable the simulation rod to be located at different positions;
   a first driving device, wherein the first driving device is connected to the movable frame and used for driving the movable frame to move relative to the fixing frame, and the first driving device is a rotary motor; and
   a transmission mechanism, wherein the transmission mechanism is connected to the rotary motor and used for changing a rotary motion into a linear motion, and the transmission mechanism is connected to the movable frame and used for driving the movable frame to move linearly relative to the fixing frame under an action of the rotary motor.

2. The anti-collision simulation device according to claim 1, further comprising a second driving device, the second driving device being connected to the simulation rod and used for driving the simulation rod to rotate.

3. The anti-collision simulation device according to claim 2, further comprising: a sensing device, a first controller and a prompter that are electrically connected; wherein
   the sensing device is disposed on the simulation rod, and used for obtaining a distance information of the simulation rod and a patient and sending the distance information to the first controller; and
   the first controller is used for controlling the prompter to send out a prompt signal according to the distance information obtained by the sensing device.

4. The anti-collision simulation device according to claim 2, further comprising: a sensing device and a second controller that is electrically connected to the second driving device and the sensing device; wherein
   the sensing device is disposed on the simulation rod, and used for obtaining a distance information of the simulation rod and a patient and sending the distance information to the second controller; and
   the second controller is used for controlling the second driving device to drive the simulation rod to run in a state according to the distance information sent by the sensing device.

5. The anti-collision simulation device according to claim 1, further comprising a sliding mechanism, wherein the fixing frame and the movable frame are slidably connected through the sliding mechanism.

6. The anti-collision simulation device according to claim 5, wherein the sliding mechanism includes a guide and a slider;
the guide is disposed on the fixing frame, and the slider is disposed on the movable frame; or, the slider is disposed on the fixing frame, and the guide is disposed on the movable frame.

7. The anti-collision simulation device according to claim 6, wherein the guide is a guide rail, and the slider is a sliding block that is able to slide in cooperation with the guide rail;
or, the guide is a guide pillar, and the slider is a guide sleeve that is able to slide in cooperation with the guide pillar.

8. The anti-collision simulation device according to claim 1 wherein the transmission mechanism includes a rotary motion member and a linear motion member that are cooperated with each other, the rotary motion member is connected to an output shaft of the rotary motor, and the linear motion member is connected to the movable frame.

9. The anti-collision simulation device according to claim 8, wherein the rotary motion member is a screw shaft, and the linear motion member is a nut that is cooperated with the screw shaft;
or, the rotary motion member is a pinion, and the linear motion member is a rack that is cooperated with the pinion.

10. The anti-collision simulation device according to claim 1, further comprising: a sensing device, a first controller and a prompter that are electrically connected, wherein
the sensing device is disposed on the simulation rod, and used for obtaining a distance information of the simulation rod and a patient and sending the distance information to the first controller; and
the first controller is used for controlling the prompter to send out a prompt signal according to the distance information obtained by the sensing device.

11. The anti-collision simulation device according to claim 1, wherein an inner side of the simulation rod facing a space enclosed by a rotation track of the simulation rod is made of a flexible material.

12. The anti-collision simulation device according to claim 1, wherein a cross section of the simulation rod is in a semi-circular shape, and an arc convex surface of the semi-circular shape is located on an inner side of the simulation rod facing a space enclosed by a rotation track of the simulation rod.

13. A radiotherapy system, comprising:
the anti-collision simulation device according to claim 1;
a radiotherapy device; and
a therapy couch; wherein
the movable frame of the anti-collision simulation device is able to move relative to the fixing frame, so as to enable the simulation rod to be located at different positions in a vertical direction relative to the therapy couch;
a space enclosed by a rotation track of the simulation rod is matched with a space in a therapy cabin of the radiotherapy device; and
the fixing frame is fixedly installed relative to the radiotherapy device.

14. The radiotherapy system according to claim 13, further comprising an anti-collision control device and a therapy couch control device that are electrically connected to each other; wherein
the anti-collision control device is used for sending different control instructions to the therapy couch control device according to different positions of the simulation rod of the anti-collision simulation device; and the therapy couch control device is used for controlling the therapy couch to move correspondingly according to the received control instructions;
or,
the anti-collision control device is used for sending a position information of the simulation rod of the anti-collision simulation device to the therapy couch control device; and the therapy couch control device is used for controlling the therapy couch to move correspondingly according to the position information.

15. The radiotherapy system according to claim 14, wherein the anti-collision control device is used for controlling a movement of the movable frame of the anti-collision simulation device to obtain the position information of the simulation rod of the anti-collision simulation device;
or,
the radiotherapy system further comprises a position detecting device used for obtaining the position information of the simulation rod of the anti-collision simulation device.

16. An anti-collision simulation device, comprising:
a supporting frame;
a simulation rod rotatably connected to the supporting frame, wherein the supporting frame includes a fixing frame and a movable frame, the simulation rod is rotatably connected to the movable frame, and the movable frame is able to move relative to the fixing frame, so as to enable the simulation rod to be located at different positions; and
a first driving device, the first driving device being connected to the movable frame and used for driving the movable frame to move relative to the fixing frame, wherein
the first driving device is a pneumatic cylinder or a hydraulic cylinder, a piston rod of the pneumatic cylinder or the hydraulic cylinder is fixedly connected to the movable frame, and a cylinder body of the pneumatic cylinder or the hydraulic cylinder is fixed relative to the fixing frame;
or, the first driving device is a linear motor, a rotor of the linear motor is fixedly connected to the movable frame, and a stator of the linear motor is fixed relative to the fixing frame.

17. An anti-collision simulation device, comprising:
a supporting frame;
a simulation rod rotatably connected to the supporting frame, wherein the supporting frame includes a fixing frame and a movable frame, the simulation rod is rotatably connected to the movable frame, and the movable frame is able to move relative to the fixing frame, so as to enable the simulation rod to be located at different positions; and
a sensing device, a first controller and a prompter that are electrically connected, wherein
the sensing device is disposed on the simulation rod, and used for obtaining a distance information of the simulation rod and a patient and sending the distance information to the first controller; and the first controller is used for controlling the prompter to send out a prompt signal according to the distance information obtained by the sensing device.

* * * * *